(12) United States Patent  (10) Patent No.: US 8,277,108 B2
Yang  (45) Date of Patent: Oct. 2, 2012

(54) STRUCTURE OF LAMP COMBINED WITH PICTURE FRAME AND ESSENCE

(76) Inventor: Chin-Sheng Yang, Tainan (TW)

( * ) Notice: Subject to any disclaimer, the term of this patent is extended or adjusted under 35 U.S.C. 154(b) by 348 days.

(21) Appl. No.: 12/762,384

(22) Filed: Apr. 19, 2010

(65) Prior Publication Data

US 2010/0271846 A1  Oct. 28, 2010

(30) Foreign Application Priority Data

Apr. 28, 2009  (TW) ................................ 98205691 A

(51) Int. Cl.
*H01R 33/00*  (2006.01)
(52) U.S. Cl. ........................................ 362/643; 362/644
(58) Field of Classification Search .................... 362/92, 362/97.1, 101, 125, 641, 643, 644
See application file for complete search history.

(56) References Cited

U.S. PATENT DOCUMENTS 4,549,250 A * 10/1985 Spector .......................... 362/101
4,714,984 A * 12/1987 Spector .......................... 362/101

\* cited by examiner

*Primary Examiner* — David V Bruce
(74) *Attorney, Agent, or Firm* — Leong C. Lei

(57) ABSTRACT

A structure of lamp is combined with a picture frame and a mass of essence. The structure includes a picture frame body that receives and holds therein a picture or photo and forms a lighting chamber that receives and holds the lamp. The lighting chamber has a wall portion in which ventilation holes are defined. The picture frame body also forms an essence compartment that receives and holds the mass of essence that gives off a scent smell. The lamp, when lit, generates heat that causes the mass of essence to give off the scent that spreads through the ventilation holes of the lighting chamber. Thus, besides receiving and holding a picture, the picture frame also provides the functions of nighttime lighting and scent spreading for improving air quality of the surroundings.

1 Claim, 3 Drawing Sheets

STRUCTURE OF LAMP COMBINED WITH PICTURE FRAME AND ESSENCE

TECHNICAL FIELD OF THE INVENTION

The present invention generally relates to a structure of lamp combined with picture frame and essence, and more particularly to a combined structure of lamp, picture frame, and essence that provide multiple interesting functions of vision, perfuming smell, and lighting, wherein a base is provided, in which electrical resistance means, light-emitting diode (LED) elements, and a mass of essence are included to cooperate with a recessed picture frame seat for inducing a flowing sense of liquid in an aqua-lamp to realize the above mentioned functions.

DESCRIPTION OF THE PRIOR ART

Almost everyone places decorations in his or her home, such as puppets or toy figurines, pictures, or picture frames positioned on desks. Such articles are used to decorate the indoor spaces, serving as a measure to improve the surrounding atmosphere. A picture frame is one of the most commonly used household decorations. A picture frame can hold a picture of any of the family members and can also serve as a frame for a drawing. The picture frames that are currently available in the market form a vision window in which a picture or a drawing can be placed and comprises a frame portion that surrounds the window. The frame portion can be of various shapes and configurations and can be made of different materials. However, those existing picture frames are limited in their functions to only decoration and picture holding. Consequently, the development and use of the picture frame is constrained.

On the other hand, there is often odor smells existing in the indoor and/or outdoor surroundings. It is often hard to smell fresh air in the modern industrialized environment, where air pollution can be found everywhere around the world. For such a reason, various perfuming devices that give off scent to the surrounding air are available in the market, including an essence lamp that burns an essence contained substance, a scent sprayer that sprays scent smell to the atmosphere, and an electrical essence lamp. These devices are selected according to the consumers' desires. However, these perfuming devices provides a single function of changing the smell that the consumers can take from the surrounding air to refresh their spirits. Further, a night lamp that is powered by being plugged into for example a wall outlet is to provide illumination for supporting users' activities in the nighttime without turning on the major lighting devices. Generally, the night lamps are lighting devices of small wattage and consuming less electricity. The commonly known configurations of night lamp include the traditional dome shape or shellfish shape, or are made in the form of puppets or cartoon figurines. With the versatile and vivid modifications of the shapes of night lamp, which realize a breakthrough of the conventional monotonous and boring design, the night lamp, besides the function of lighting, can also have a function decoration. It is thus desired to combine the decorative night lamp with the functions of air quality improvement or perfuming and further added with a picture frame to hold and display a picture, and it is believed that such a combined structure will be prevailing in the future consumer market. The present invention thus aims to provide a structure of lamp combined with picture frame and essence, which will provides functions in respect of vision, smell, and decoration.

SUMMARY OF THE INVENTION

Thus, the present invention provides a structure of lamp combined with picture frame and essence. The structure comprises a picture frame body that receives and holds therein a picture or photo and forms a lighting chamber that receives and holds the lamp. The lighting chamber has a wall portion in which ventilation holes are defined. The picture time body also forms an essence compartment that receives and holds the mass of essence that gives off a scent smell. The lamp, when lit, generates heat that causes the mass of essence to give off the scent that spreads through the ventilation holes of the lighting chamber. Thus, besides receiving and holding a picture, the picture frame also provides the functions of nighttime lighting and scent spreading for improving air quality of the surroundings.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
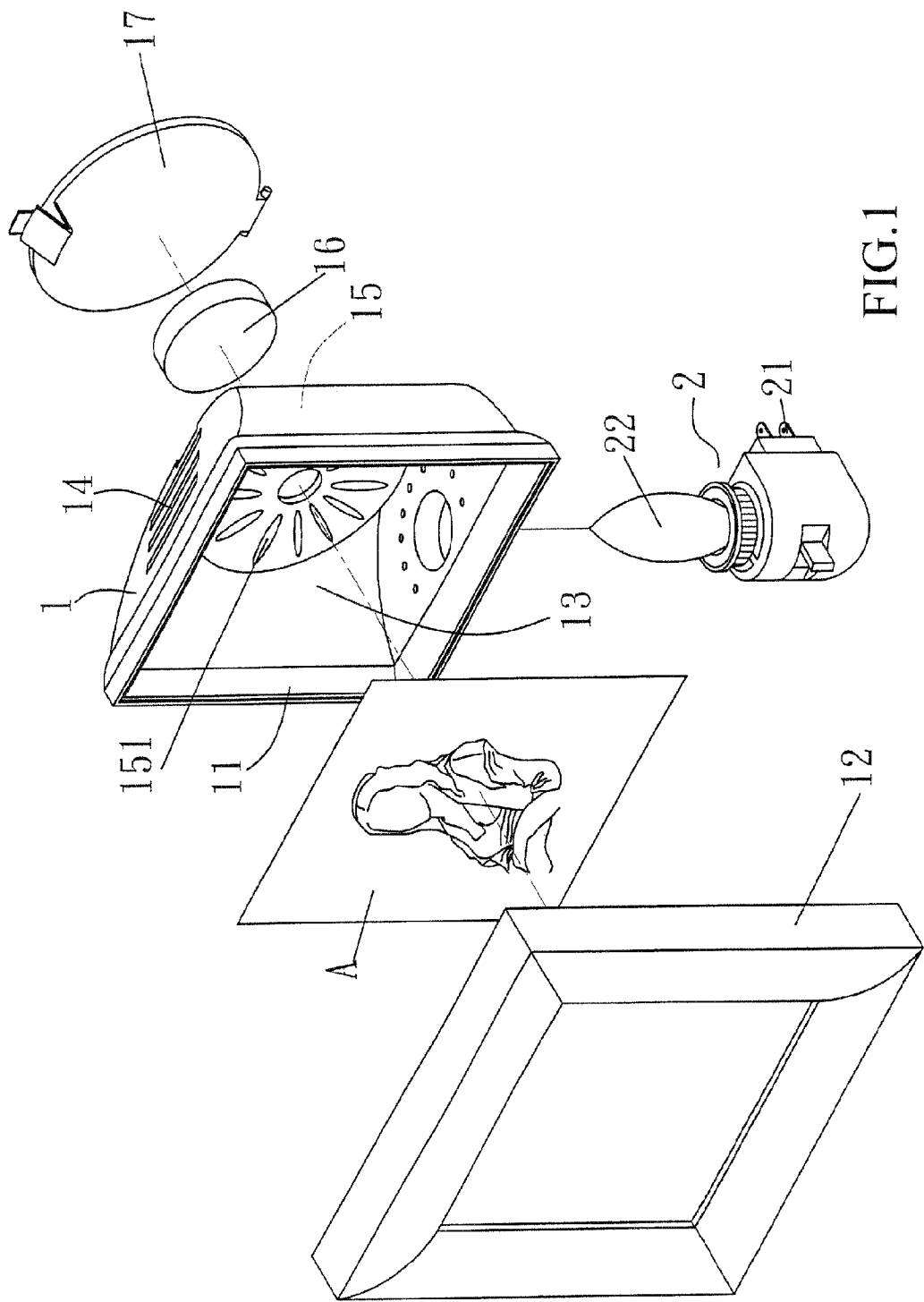
FIG. 1 is an exploded view of the present invention.

Referring to FIG. 1, which shows an exploded view of a structure of lamp combined with picture frame and essence, the structure comprises a picture frame body 1 and a lamp assembly 2.

The picture frame body 1, which is in the form of a hollow casing, has an opening defining a receptacle 11 that selectively receives and holds therein a picture or photo A. A frame-like cover 12 is fit to the opening 11. The picture frame body 1 forms therein a lighting chamber 13 that is delimited by surrounding wall portions that constitute in part the casing like body 1. Ventilation holes 14 are defined in the wall portions. The picture frame body 1 also forms an essence compartment 15 adjacent to and preferably spaced from the lighting chamber 13. The essence compartment 15 has through holes 151 forms in a wall thereof, preferably in a partition wall separating the lighting chamber 13 and the essence compartment 15. The essence compartment 15 selectively receives and holds therein a mass of essence 16. The essence compartment 15 is provided with a lid 17 that openably closes the essence compartment 15.

The lamp assembly 2 is composed of a power connection portion 21, such as a plug portion, that is selectively set in contact with a power source and an incandescent bulb 22. The incandescent bulb 22 is received and retained in the lighting chamber 13 of the picture frame body 1.

Figure 2:
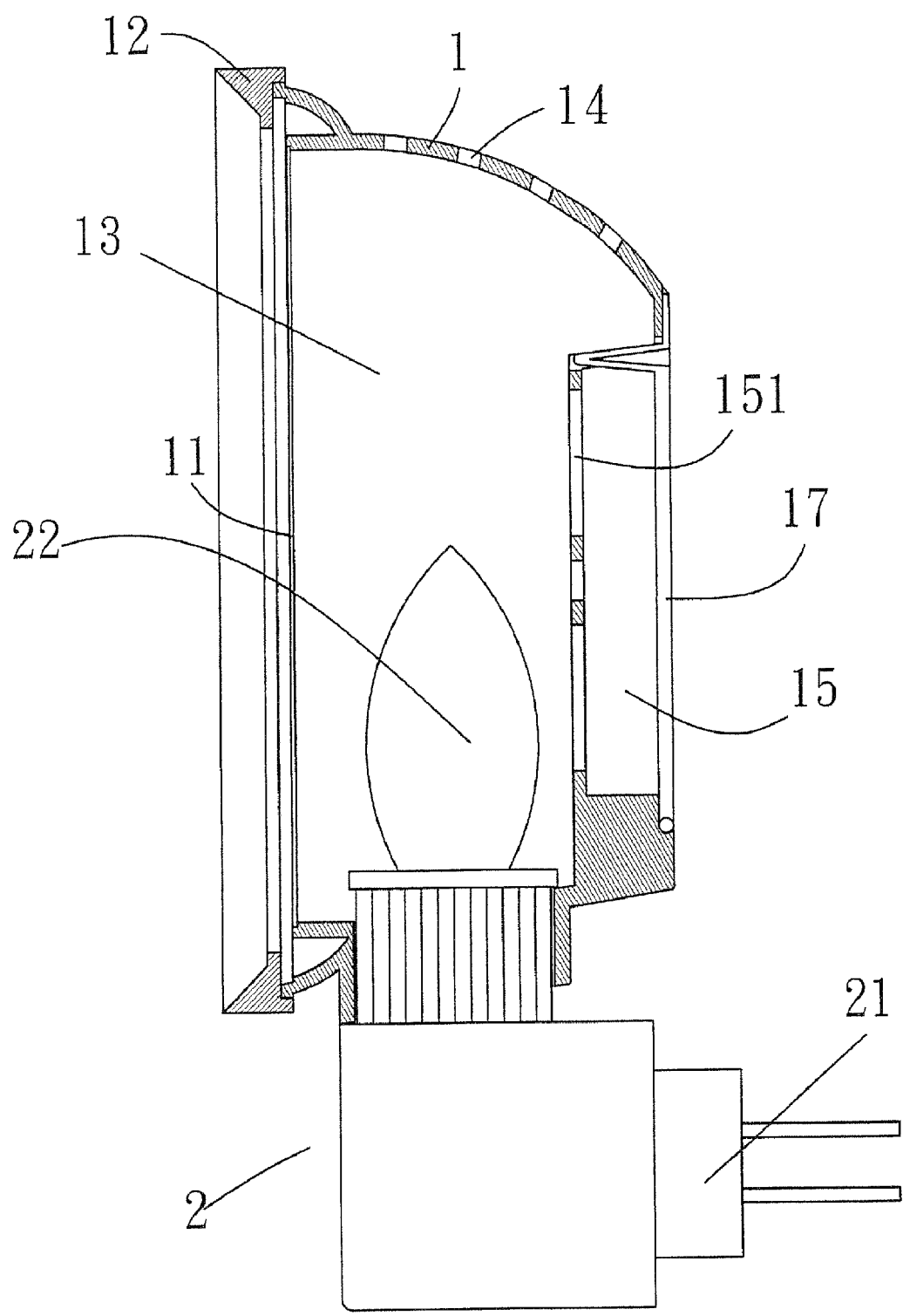
FIG. 2 is a cross-sectional view of the present invention.
Figure 3:
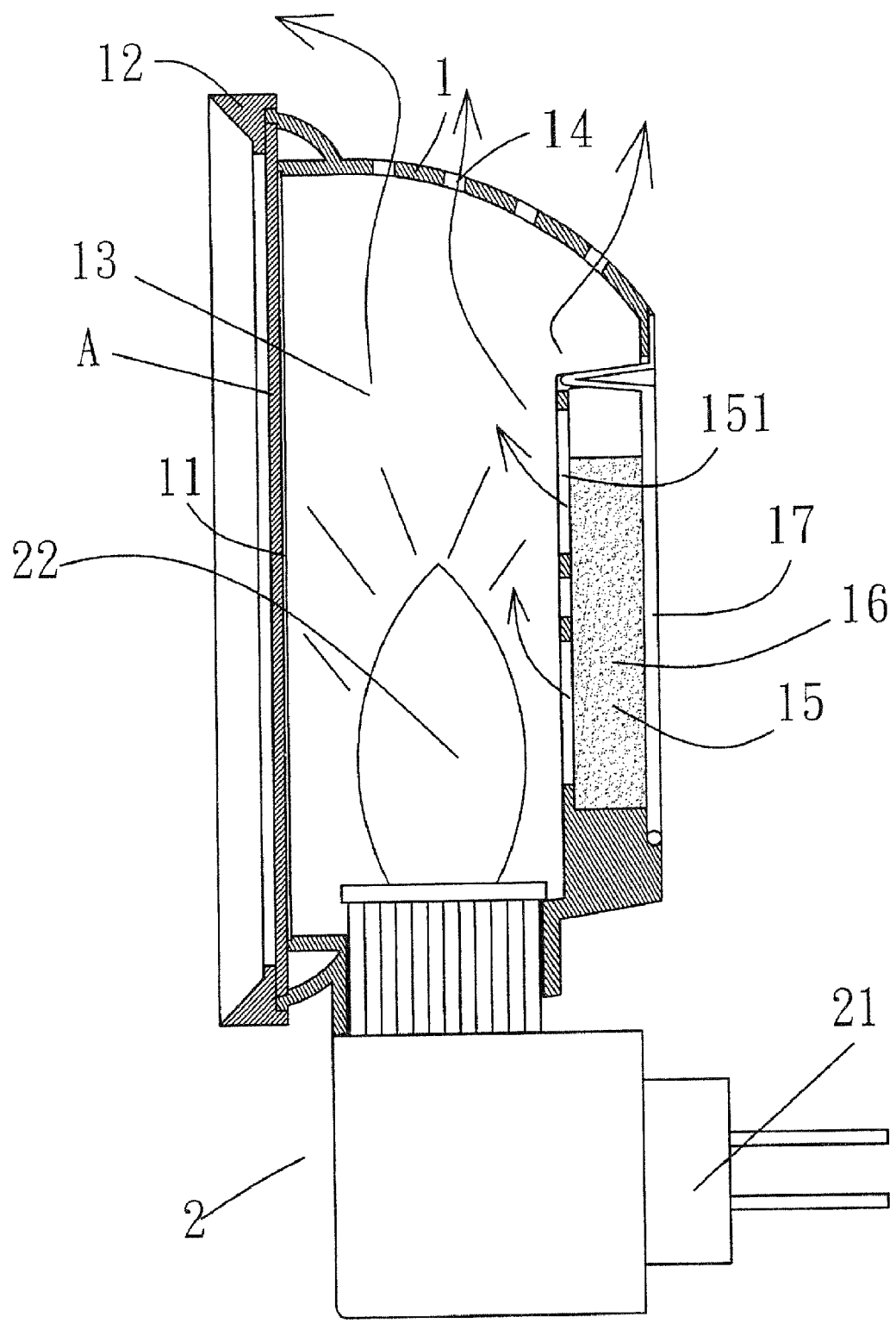
FIG. 3 is also a cross-sectional view of the present invention illustrating the use of the present invention.

Further referring to FIGS. 2 and 3, which show cross-sectional views of the structure of lamp combined with picture frame and essence according to the present invention, to use the lamp of the present invention, the lamp assembly 2 is first set in the lighting chamber 13 of the picture frame body 1 so as to retain the incandescent bulb 22 in the lighting chamber 13 of the picture frame body 1. Afterwards, a picture or photo A is put into and held in the opening receptacle 11 of the picture frame body 1 and the cover 12 is fit to the opening 11 to form a configuration of picture frame. Then, the mass of essence 16 is deposited into the essence compartment 15 of the picture frame body 1 and the lid 17 is set to close the essence compartment 15. Finally, the plug portion 21 of the lamp assembly 2 is set in electric engagement with an external power source to supply electricity to light up the incandescent bulb 22. The incandescent bulb 22, once lit, gives off heat that evaporates the essence 16 deposited in the essence compartment 15 so that scent may spread through the ventilation holes 14 of the lighting chamber 13. In this way, besides holding and displaying a picture or photo, the picture frame according to the present invention also provides lighting that help illumination in nighttime and gives off scent that improves the surrounding atmosphere.

In summary, from the constituent components that have been described above and the functions thereof, the present invention offers the following advantages:

(1) The structure of lamp combined with picture frame and essence according to the present invention comprises an incandescent bulb that is arranged within a picture frame to provide lighting, so that the picture frame also functions to provide nighttime illumination.

(2) The picture frame according to the present invention receives, holds, and displays a picture or photo, whereby besides the lighting effect described above, the present invention also provides the function of picture frame that holds and displays a picture or photo.

(3) The structure of lamp combined with picture frame and essence according to the present invention comprises a picture frame body that forms an essence compartment receiving and holding therein a mass of essence that gives off scent smell, whereby besides the lighting effect described above, the picture frame body of the present invention also functions to spread scent smell through the ventilation holes, which helps improving air quality of the surroundings, allowing the present invention to be practiced in a versatile manners.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A structure of lamp combined with picture frame and essence, comprising a picture frame body and a lamp assembly, wherein:

the picture frame body forms an opening that serves as a receptacle for receiving and holding therein a picture and comprises a cover that is detachably fit to the opening, the picture frame body forming therein a lighting chamber that has a wall portion in which a ventilation hole is defined, the picture frame also forming an essence compartment having a wall forming a through hole, the essence compartment receiving and holding therein a mass of essence that gives off a scent smell, the essence compartment being provided with a lid that closes the essence compartment; and the lamp assembly comprises a power connection portion adapted to be in engagement with an external power source and an incandescent bulb that is received and held in the lighting chamber of the picture frame body.

* * * * *